(12) United States Patent
Vyas

(10) Patent No.: US 6,492,398 B1
(45) Date of Patent: Dec. 10, 2002

(54) THIAZOLOINDOLINONE COMPOUNDS

(75) Inventor: Ambrish Vyas, Durham, NC (US)

(73) Assignee: SmithKline Beechman Corporation, Philadelphia, PA (US)

( * ) Notice: Subject to any disclaimer, the term of this patent is extended or adjusted under 35 U.S.C. 154(b) by 0 days.

(21) Appl. No.: 09/914,420

(22) PCT Filed: Mar. 1, 2000

(86) PCT No.: PCT/US00/05192

§ 371 (c)(1),
(2), (4) Date: Aug. 28, 2001

(87) PCT Pub. No.: WO00/52013

PCT Pub. Date: Sep. 8, 2000

(30) Foreign Application Priority Data

Mar. 4, 1999 (GB) .............................. 9904930

(51) Int. Cl.$^7$ ...................... A61K 31/425; A61K 31/44; C07D 513/04
(52) U.S. Cl. .................................... 514/338; 546/276.1
(58) Field of Search ........................ 546/270.1; 514/338

(56) References Cited

U.S. PATENT DOCUMENTS

| | | | |
|---|---|---|---|
| 5,051,417 A | 9/1991 | Nadler et al. ............. | 514/222.5 |
| 5,057,538 A | 10/1991 | Shiraishi et al. ............ | 514/521 |
| 5,089,516 A | 2/1992 | Shiraishi et al. ............ | 514/404 |
| 5,124,342 A | 6/1992 | Kerdesky et al. ........... | 514/369 |
| 5,202,341 A | 4/1993 | Shiraishi et al. ............ | 514/369 |
| 5,374,652 A | 12/1994 | Buzzetti et al. ............. | 514/418 |
| 5,441,880 A | 8/1995 | Beach et al. ................. | 435/193 |
| 5,443,962 A | 8/1995 | Draetta et al. ................ | 435/29 |
| 5,449,775 A | 9/1995 | Roberts et al. ............. | 540/202 |
| 5,488,057 A | 1/1996 | Buzzetti et al. ............. | 514/312 |
| 5,627,207 A | 5/1997 | Buzzetti et al. ............. | 514/520 |
| 5,672,508 A | 9/1997 | Gyruis et al. ............ | 435/320.1 |
| 5,756,335 A | 5/1998 | Beach et al. ................. | 435/197 |
| 5,770,423 A | 6/1998 | Beach et al. ................. | 435/197 |
| 5,861,259 A | 1/1999 | Roberts et al. .............. | 435/7.1 |

FOREIGN PATENT DOCUMENTS

| | | |
|---|---|---|
| EP | 0 436 333 A2 | 12/1990 |
| EP | 0 503 49 A1 | 2/1992 |
| EP | 0 503 349 B1 | 2/1992 |
| EP | 0 788 890 A1 | 2/1996 |
| WO | 93/01182 | 7/1992 |
| WO | 92/20796 A2 | 11/1992 |
| WO | 93/10242 | 11/1992 |
| WO | 94/28914 | 6/1993 |
| WO | 93/24514 | 12/1993 |
| WO | 94/23029 | 3/1994 |
| WO | 95/01349 | 5/1994 |
| WO | 96/00226 | 6/1994 |
| WO | 96/16964 | 10/1995 |
| WO | 96/22976 | 12/1995 |
| WO | 96/32380 | 3/1996 |
| WO | 96/40116 | 6/1996 |
| WO | 97/25986 | 1/1997 |
| WO | 97/36867 | 2/1997 |
| WO | 98/07695 | 8/1997 |
| WO | 98/07835 | 8/1997 |
| WO | 99/15500 | * 4/1999 |

OTHER PUBLICATIONS

Rozegurt, Current Opinon in Cell Biology, 1992, 4, pp. 161–165.
Wilks, Progress in Growth Factor Research, 1990, 2. Pp. 97–111.
Hanks, et al., Science, 1988, 241, pp. 42–52.
Crews and Erickson, Cell, 1993, 74, pp. 215–217.
Ihle et al., Trends in Biochemical Sciences, 1994, 19, pp 222–7.
Pelech and Sanghera, Trends in Cell Biochemical Sciences, 1992, 17, pp. 233–238.
Massague and Roberts, Current Opinion in Cell Biology, 1995, 7, pp. 769–772.
Myerson et al., EMBO Journal, 1992, 11, pp. 2909–2917.
Draetta, Trends in Cell Biology, 1993, 3, pp. 287–289.
Murray and Kirschner, Nature, 1989, 339, pp. 275–280.
Solomon et al., Molecular Biology of the Cell, 1992, 3, pp. 13–27.
Ducommun et al., EMBO Journal, 1991, 10, pp. 3311–3319.
Gautier et al., Nature, 1989, 339, pp. 626–629.
Gould and Nurse, Nature, 1989, 342, pp. 39–45.
Krek and Nigg, EMBO Journal, 1991, 10, pp. 3331–3341.
Solomon et al., Cell, 1990, 63, pp. 1013–1024.
Pines, Trends in Biochemical Sciences, 1993, 18, pp. 195–197.
Sherr, Cell, 1993, 73, pp. 1059–1065.
Matsushime et al., Molecular & Cellular Biology, 1994,14, pp. 2066–2076.
Ohtsubo and Roberts, Science, 1993, 259, pp. 1908–1912.
Quelle et al., Genes & Development, 1993, 7, pp. 1559–1571.
Resnitzky et al., Molecular & Cellular Biology, 1994, 14, pp. 1669–1679.
Girard et al., Cell, 1991, 67, pp. 1169–1179.
Pagano et al., EMBO Journal, 1992, 11, pp. 961–971.
Rosenblatt et al., Proceedings of the National Academy of Science USA, 1992, 89, pp. 2824–2828.

(List continued on next page.)

Primary Examiner—Bernard Dentz
(74) Attorney, Agent, or Firm—John L. Lemanowicz

(57) ABSTRACT

Thiazole-indole compounds useful as cyclin dependent kinase 11 inhibitors, for preventing/reducing the severity of epithelial cytotoxicity side-effects (e.g., alopecia, plantar-palmar syndrome, mucositis) induced by chemoptherapy and/or radiation therapy in a patient receiving such therapy.

50 Claims, 2 Drawing Sheets

OTHER PUBLICATIONS

Figure 1:
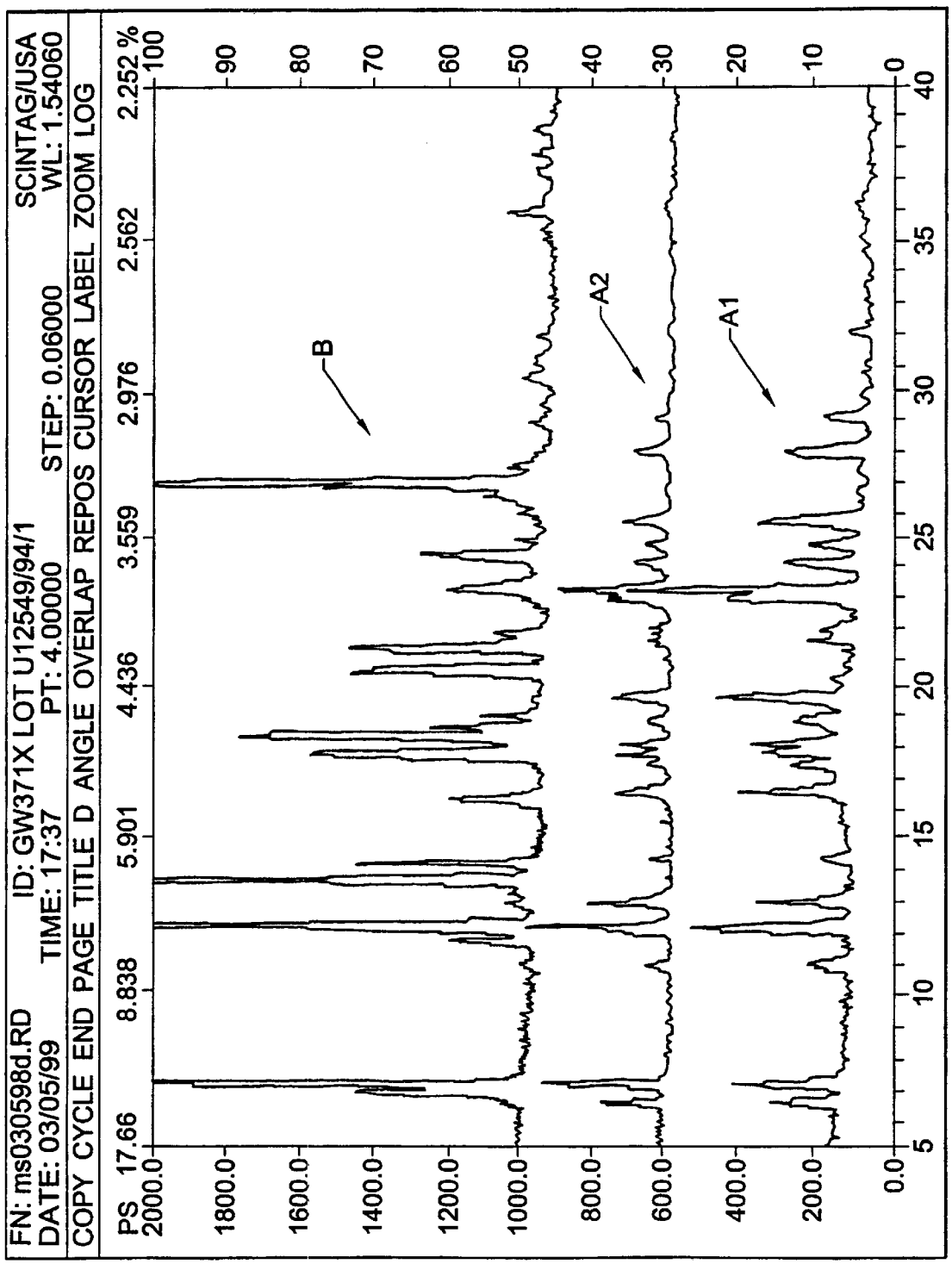

Walker and Maller, Nature, 1991, 354, pp. 314–317.
Zindy et al., Biochemical & Biophysical Research Communications, 1992, 182, pp. 1144–1154.
Pines, Current Opinion in Cell Biology, 1992, 4, pp. 144–148.
Lees, Current Opinion in Cell Biology, 1995, 7, pp. 773–780.
Hunter and Pines, Cell, 1994, 79, pp. 573–582.
Brickell, Critical Reviews in Oncogenesis, 1992, 3, pp. 401–446.
Courtneidge, Seminars in Cancer Biology, 1994, 5, pp. 239–246.
Powis, Pharmacology & Therapeutics, 1994, 62, pp. 57–95.
Buchdunger et al., Proc. Nat. Acad. Sci USA, vol. 92, 1995, pp. 2258–2262.
Hosoi et al., Journal of Biochemistry (Toyko), 1995, 117, pp. 741–749.
Aplin et al., Journal of Neurochemistry, 1996, 67, pp. 699–707.
Tanaka et al., Nature, 1996, 383, pp. 528–531.
Borthwick et al., Biochemical & Biophysical Research Communications, 1995, 210, pp. 738–745.
Badger et al., Journal of Pharmacology & Experimental Therapeutics, 1996, 279, pp. 1453–1461.
Shawyer et al., Drug Discovery Today, 1997, 2, pp. 50–63.
He et al., Journal of Virology, 1997, 71, pp. 405–411.
Myers et al., Bioorganic & Medicinal Chemistry Letters, 1997, 7, pp. 421–424.
Vousden, FASEB Journal, 1993, 7, pp. 872–879.
Stone et al., Cancer Research, 1996, 56, pp. 440–452.
Perkins et al., Science, 1997, 275, pp. 523–527.
Baeuerle and Henkel, Annual Review of Immunology, 1994, 12, pp. 141–179.
Beg and Baltimore, Science, 1996, 274, pp. 782–784.
Wang et al., Science, 1996, 274, pp. 784–787.
Van Antwerp et al., Science, 1996, 274, pp. 787–789.
Armstrong, Clinical Infectious Diseases, 1993, 16, pp. 1–7.
Osmani et al., EMBO Journal, 1991, 10, pp. 2669–2679.
Kohn et al., Journal of Cellular Biochemistry, 54, 1994, pp. 440–452.
Osmani et al., Cell, vol. 67, Oct. 18, 1991, pp. 283–291.
Mohammed Kamel et al., "Monoazo Metal Complex Forming Dyes Part v Dyes Derived form Isatin," J. Chem. U.A.R. 9, No. 2, 139–144 (1996).
Vishnu J. Ram, et al., "Pesticidal mannich Bases Derived from Isatinimines," J Heterocycle Chem. pp. 1367–1369, vol. 23, Sep.–Oct. 1986.
Xiaoyun Wu et al., "Chemical Constiuents of Isatis Indigotica, " Planta Medica, pp. 55–57, 1997.
Cline, B.W., "Prevention of Chemotherapy–Induced Alopecia: A Review of the Literature," Cancer/Nursing, Jun. 1984, pp. 221–227.
Gray, N.S. et al., "Exploiting Chemical Libraries, Structure, and Genomics in the Search for Kinase Inhibitors," Sicence, vol. 281, Jul. 24, 1998, pp. 533–538.
Hussein, A.M., "Chemotherapy–Induced Alopecia: New Developments," Southern Medical Journal, May 1993, vol. 86, No. 5, pp. 489–496.
Hussein, A.M., "Protection from Chemotherapy–Induced Alopecia in a Rat Model," Science, vol. 249, Sep. 28, 1990, pp. 1564–1566.
Lauer, A.C. et al., "Transfollicular Drug Delivery," Pharmaceutical Research, vol. 12, No. 2, 1995, pp. 179–186.
Li, L., et al., "The Feasibility of Targeted Selective Gene Therapy of the Hair Follicle," Nature Medicine, vol. 1, No. 7, Jul. 1995, pp. 705–706.
Pallumbo, Giuseppe A., et al., "The Tyrphostin AG17 Induces Apoptosis and Inhibition of cdk2 Activity in a Lymphoma Cell Line that Overexpresses bcl–2," Cancer Research, 57, Jun. 15, 1997, pp. 2434–2439.
Sedlacek, Hans H., et al., "Flavopiridol (L86 82875; NSC 649890), a New Kinase Inhibitor for Tumor Therapy," International Journal of Oncology, vol. 9, 1996, pp. 1143–1168.
Toledo, Leticia M. et al., "Structures of Staurosporine Bound on CDK2 and cAPK–New Tools for Structure–based Designed of Protein Kinase Inhibitors," Structure, 1997, vol. 5, No. 12, pp. 1551–1556.

\* cited by examiner

THIAZOLOINDOLINONE COMPOUNDS

This application is filed pursuant to 35 U.S.C. § 371 as a United States National Phase Application of International Application No. PCT/US00/05192 filed Mar. 1, 2000, which claims priority from United Kingdom 9904930.6 filed Mar. 4, 1999.

The present invention relates generally to thiazolindolinone compounds having utility as cyclin dependent kinase II inhibitors useful, inter alia, for preventing/reducing the severity of epithelial cytotoxic effects (e.g., alopecia, plantar-paimar syndrome, and mucositis) incident to chemotherapy and/or radiation therapy. The present invention also relates to the synthesis of such compounds, and to formulations containing such compounds as pharmacological compositions for preventing/reducing the severity of epithelial cytotoxic effects in a patient subjected to corresponding chemotherapy and/or radiation therapy treatment.

BACKGROUND OF THE INVENTION

Protein kinases play a critical role in the control of cell growth and differentiation and are key mediators of cellular signals leading to the production of growth factors and cytokines. See, for example, Schlessinger and Ullrich, *Neuron* 1992, 9, 383. A partial, non-limiting, list of such kinases includes abl, ARaf, ATK, ATM, bcr-abl, Bik, BRaf, Brk, Btk, CDK1, CDK2, CDK3, CDK4, CDK5, CDK6, CDK7, CDK8, CDK9, cfms, c-fms, c-kit, c-met, cRaf1, CSF1R, CSK, c-src, EGFR, ErbB2, ErbB3, ErbB4, ERK, ERK1, ERK2, Fak, fes, FGFRI, FGFR2, FGFR3, FGFR4, FGFR5, Fgr, FLK4, Fps, Frk, Fyn, GSK, gsk3a, gsk3b, Hck, IGF-1R, IKK, IKK1, IKK2, IKK3, INS-R, Integrin-linkedkinase, Jak, JAK1, JAK2, JAK3, JNK, JNK, Lck, Lyn, MEK, MEK1, MEK2, p38, PDGFR, PIK, PKB1, PKB2, PKB3, PKC, PKCa, PKCb, PKCd, PKCe, PKCg, PKCI, PKCm, PKCz, PLK1, Polo-like kinase, PYK2, tie$_1$, tie$_2$, TrkA, TrkB, TrkC, UL13, UL97, VEGF-R1, VEGF-R2, Yes and Zap70. Protein kinases have been implicated as targets in central nervous system disorders such as Alzheimers (Mandelkow, E. M. et al. *FEBS Lett*. 1992, 314, 315. Sengupta, A. et al. *Mol. Cell. Biochem*. 1997, 167,99), pain sensation (Yashpal, K. *J. Neurosci*. 1995, 15, 3263–72), inflammatory disorders such as arthritis (Badger, *J. Pharm. Exp. Ther*. 1996, 279, 1453), psoriasis (Dvir, et al, *J. Cell Biol*. 1991, 113, 857), and chronic obstructive pulmonary disease, bone diseases such as osteoporosis (Tanaka et al, *Nature*, 1996, 383, 528), cancer (Hunter and Pines, *Cell* 1994, 79, 573), atherosclerosis (Hajjar and Pomerantz, *FASEB J*. 1992, 6, 2933), thrombosis (Salari, *FEBS* 1990, 263, 104), metabolic disorders such as diabetes (Borthwick, A.C. et al. *Biochem. Biophys. Res. Commun*. 1995, 210, 738), blood vessel proliferative disorders such as angiogenesis (Strawn et al *Cancer Res*. 1996, 56, 3540; Jackson et al *J. Pharm. Exp. Ther*. 1998, 284, 687), restenosis (Buchdunger et al, *Proc, Nat Acad. Sci USA* 1991, 92, 2258), autoimmune diseases and transplant rejection (Bolen and Brugge, *Ann. Rev. Immunol*. 1997, 15, 371) and infectious diseases such as viral (Littler, E.*Nature* 1992, 358, 160), and fungal infections (Lum, R. T. PCT Int. Appl., WO 9805335 A1 980212).

Chemotherapeutic techniques and radiation therapy techniques are well established in the treatment of neoplastic conditions of various types. As concomitant side-effects to the administration of chemotherapy and/or radiation therapy, the patient may experience severe host epithelial cell toxicity. The consequences of damage to the proliferating epithelium induced by chemotherapy frequently include hair loss (alopecia), plantar-palmar syndrome and mucositis; such side effects, especially mucositis, are also known to occur as a result of radiation therapy. These side-effect conditions may be of varying severity, depending on the type, dosages and dosing schedule of the respective chemotherapy and/or radiation therapy involved.

SUMMARY OF THE INVENTION

The present invention relates to the compound:

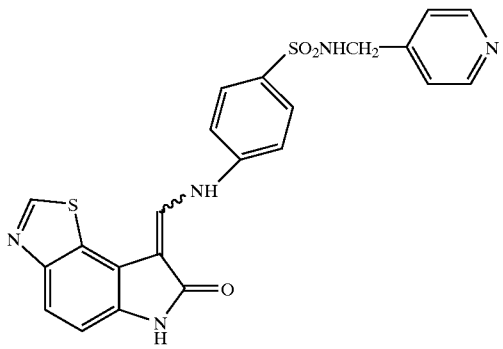

in one or more of the variant forms hereinafter more fully described.

In one aspect, the present invention provides a novel approach to preventing/reducing the severity of epithelial cytotoxicity side-effects of chemotherapy and/or radiation therapy, in a subject receiving such therapy, by administering to the subject an effective amount of one or more of such variant forms of the above thiazoliridolinone compound, as hereinafter more fully described.

Epithelial cytotoxicity side-effects that can be preventedir educed in severity in this manner include alopecia, plantar-palmar syndrome and/or mucositis is induced by chemotherapy and/or radiation therapy.

Variant species of such thiazolindolinone compound

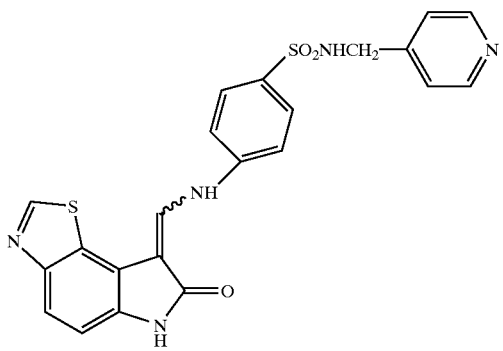

include the various forms, which are described in the ensuing discussion and characterised with reference to their melting points, x-ray diffraction crystallographic spectra, solubilities in solvent media, and methods of synthesis.

The invention also relates in another aspect to methods for preparing various forms of such thiazolindolinone compound.

A further aspect of the invention relates to a pharmaceutical composition comprising (a) at least one of the aforementioned forms of such thiazolindolinone compound, in an amount that is effective in preventing/reducing the severity of epithelial cell toxicity side effects induced by the administration of chemotherapy and/or radiation therapy, and (b) one or more pharmaceutically acceptable carriers, excipients or diluents.

Other aspects, features and advantages of the invention will be more fully apparent from the ensuing disclosure and appended claims.

DETAILED DESCRIPTION OF THE INVENTION, AND PREFERRED EMBODIMENTS THEREOF

The present invention provides a thiazolindolinone compound having various forms that are useful as cyclin dependent kinase inhibitors.

The thiazolindotinone compound has the formula:

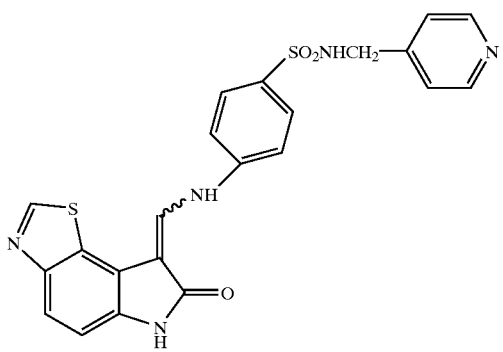

and may be prepared in variant forms, Forms A, B and C, as described more fully hereinafter.

A generalized synthesis scheme (Scheme 1) is set out below for the thiazolindolinone compound of the invention, and is described more fully in the subsequent Examples herein.

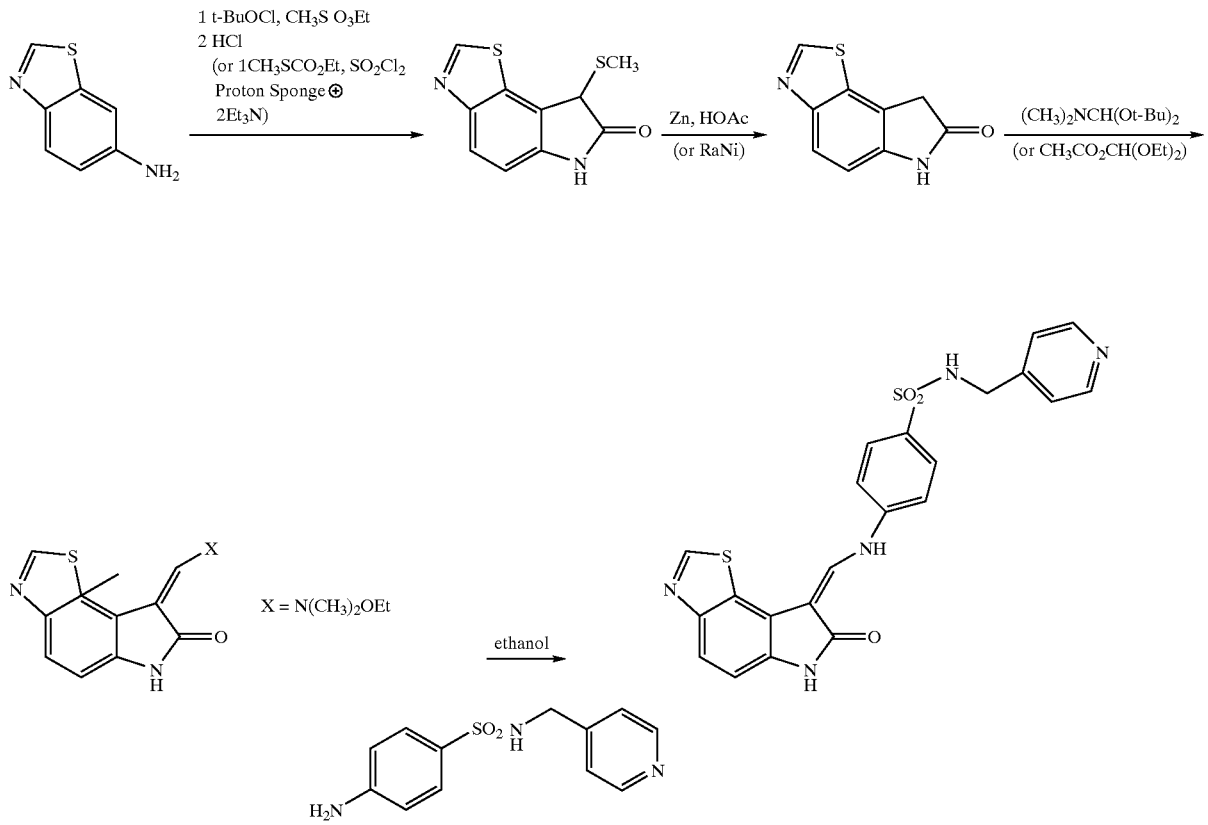

-continued

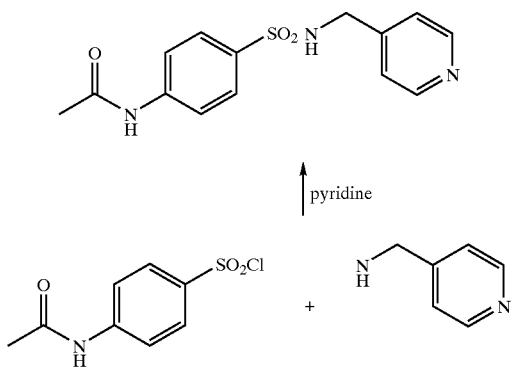

The resulting product of such synthesis, 4-{[7-oxo-6,7-dihydro-8H-[1,3]thiazolo[5,4-e]indol-8-ylidene)methyl]amino}N-(4-pyridinylmethyl)-benzene sulfonamide, can be recovered from the synthesis reaction system and thereafter submitted to recrystallization using a specific solvent species, to yield a corresponding desired form of the compound for ultimate use, as hereinafter described.

The resulting form of the compound may then be formulated as the active ingredient in a pharmaceutically acceptable composition, for topical or otherwise non-systemic administration to a subject (e.g., a mammalian subject such as a human subject), to prevent/reduce the severity of epithelial cytotoxicity side effects (e.g., alopecia, plantar-palmar syndrome, and/or mucocitis) induced by chemotherapy and/or radiation therapy being administered to the subject.

To prevent/reduce the severity of alopecia induced by chemotherapy and/or radiation therapy in a subject receiving such therapy, the thiazolindolinone compound of the invention in a suitable variant form is preferably administered topically to the corporeal locus that is susceptible to alopecia, such as the head (e.g., the scalp, eyebrow regions, beard and mustache areas, etc.).

For such topical application, the CDK2 inhibitor compound may be formulated in a topical administration formulation by combination of the compound with a selected pharmaceutically acceptable vehicle (carrier, diluent or excipient), with the amount of the compound being sufficient to achieve the prevention or reduction in severity of the alopecia side effect, when administered in accordance with an appropriately designed treatment protocol. The formulation can be in any useful dosage unit form for corresponding administration.

Formulations of the thiazolindolinone compound may be constituted and administered in any other suitable manner, such as in a liquid formulation for aerosolized spray administration to the head region of a subject susceptible to chemotherapy-induced alopecia, or by a dermal patch or dressing containing the CDK2 inhibitor formulation in a releasable form, for positioning on the head in contact with the area of susceptibility.

The formulation may alternatively be formulated as a lotion, salve, gel, foam, paste, oil, creme, or other suitable form, for administration to the appropriate corporeal locus, e.g., to the scalp or other area of the head for preventing/reducing the severity of alopecia, with initial administration being followed by massage, brushing, or toweling to distribute the formulation on the scalp evenly for uniformity of therapeutic effect.

As one example of compositions that may be used for topical adminstration of the CDK2 inhibitor agents of the invention to the corporeal locus of a subject receiving chemotherapy and/or radiation therapy, a formulation of the type described in Tata, S., et al., Relative Influence of Ethanol and Propylene Glycol Cosolvents on Deposition of Minoxidil into the Skin, Journal of Pharmaceutical Sciences, Vol. 83, No. 10, October 1994, pp. 1508–1510, may be employed, the entire disclosure of which is incorporated herein by reference. Such a formulation may comprise a 2% solution of the active ingredient in 60% ethanol, 20% propylene glycol and 20% water, for topical administration of the solution to the scalp.

Still other formulations that may be usefully employed for topical administration of the CDK2 inhibitor agents of the invention, include the formulations identified in U.S. Pat. Nos. 5,849,733; 5,807,698; 5,625,031; and 5,486,509, the disclosures of which are incorporated herein by reference in their entireties.

Additional illustrative examples of formulations that may be usefully employed for the topical administration of the CDK2 inhibitor agent of the invention include: the lipid based formulations described in Hoffman, R. M., et al., Liposomes Can Specifically Target Entrapped Melanin To Hair Follicles in Histocultured Skin, In Vivo Cell. Dev. Biol., Vol. 29A: 192–194, March 1993, and in Niemiec, S. M., et al., Influence of Nonionic Liposomal Composition on Topical Delivery of Peptide Drugs into Pilosebaceous Units: An in Vivo Study Using the Hamster Ear Model, Pharmaceutical Research, Vol. 12, No. 8, 1995, pp. 1184–1188; and the polymeric microsphere formulations described in Rolland, A., et al., Site-Specific Drug Delivery to Pilosebaceous Structures Using Polymeric Microspheres, Pharmaceutical Research, Vol. 10, No. 12, 1993, pp. 1738–1744.

The formulation may be constituted to provide an appropriate dose for a desired dosing schedule. The dosage and dosage schedule may be readily determined for a given subject, within the skill of the art, based on the character of the chemotherapy and/or radiation therapy being employed.

Analogous considerations apply to the formulation and administration of the CDK2 inhibitor for prevention/reduction in severity of plantar-palmar syndrome, involving topical administration to the areas of the hands and feet susceptible to the syndrome as a side-effect of chemotherapy and/or radiation therapy.

For preventing/reducing the severity of mucositis, the cyclin dependent kinase II inhibitor may be formulated in a suitable topical formulation for application to the oral cavity mucosa. Illustrative delivery systems for the cyclin dependent kinase II inhibitor of the invention, as used to combat mucositis, include the formulations and delivery techniques described in Cullinan U.S. Pat. No. 5,496,828 issued Mar. 5, 1996 for "Methods of Inhibiting Ulcerative Mucositis." Useful formulations may include the active ingredient and excipients, diluents, or carriers, formed into tablets, capsules, sprays, mouthwashes, lozenges, troches, pastilles, lollipops, suspensions, powders and the like, for application to the mucosa of the oral cavity. cceptable daily dosages of the CDK2 inhibitor for preventing/reducing the severity of epithtelial cytotoxicity side effects induced by chemotherapy and/or radiation therapy, may be from about 0.1 to about 1000 mg/day, and preferably from about 50 to about 200 mg/day.

The cyclin dependent kinase II inhibitor in the preferred practice of the invention is administered contemporaneously with the chemotherapy and/or radiation therapy treatment (i.e., simultaneously with, or sufficiently near in time to, the chemotherapy and/or radiation therapy, so as to achieve a preventative or ameliorative effect on the therapy-induced epithelial cytotoxicity side effect that would otherwise be presented in the absence of the CDK2 inhibitor). The chemotherapy and/or radiation therapy may be of any appropriate type for the neoplastic condition, or other disease state or condition, of the patient being treated. As an illustrative example, the chemotherapy may comprise administration of chemotherapeutic agents, including cycle-specific agents (such as cytosine arabinoside (ARA-C)) and non-cycle-specific agents (such as Cytoxan), individually or in combination with one another.

The cyclin dependent kinase II inhibitor in one embodiment of the invention is administered 1–4 times in a chemotherapeutic cycle, as a cytoprotective composition for preventing/reducing the severity of epithelial cytotoxicity side effects such as alopecia, plantar-palmar syndrome and/or mucositis, in a subject receiving chemotherapy and/or radiation therapy.

In the specific application of preventing/reducing the severity of chemotherapy-induced alopecia, the cyclin dependent kinase II inhibitor effects a desired temporary arrest of the hair follicle cell cycle by inhibition of cyclin dependent kinase II activity. For such purpose, the inhibitor agent, formulated in a suitable topically administerable formulation, may be applied 1–2 times or more per chemotherapeutic cycle prior to and during the time of administration of chemotherapy, in one preferred specific embodiment.

In one preferred aspect of the invention, cyclin dependent kinase II inhibitor agents that are topically administerable to prevent/reduce the severity of chemotherapy-induced alopecia, are assessed for efficacy and selected for use based on the following characteristics:

(1) an IC50 value of less than 2.5 nanoMolar and preferably less than 20 nanoMolar against CDK2;
(2) an IC50 value of less than 1.5 microMolar and preferably less than 5 microMolar in a G1 checkpoint assay;
(3) exhibition of reproducible protection in a babyrat alopecia model using at least 2 different cytotoxic regimens one of which includes an alkylating agent (e.g., a regimen involving doxorubicin/cyclophosphamide (anthracyclin/alkylating agent), etoposide (topoisomerase II inhibitor), taxol, etc.);
(4) a topical dose of 10 mg/kg of body weight of the subject yielding a plasma concentration of less than 15 nanoMolar, and preferably a systemic exposure to less than 0.01 of the IC50 concentration for protection of the HT29 tumour cell line;
(5) an acceptable dermal irritation profile; and
(6) suitability for the particular topical formulation to be employed (in terms of compatibility, bioavailability, etc.).

The compound of the invention, in a suitable variant form, may correspondingly be formulated for topical administration to prevent/reduce the severity of plantar/palmar syndrome, in a suitable dosing and treatment regimen for the patient receiving chemotherapy and/or radiation therapy.

For the prevention/reduction of severity of mucositis in a patient receiving chemotherapy and/or radiation therapy, the compound of the invention in an appropriate form is preferably formulated for topical administration to the oral cavity mucosa, in a mouthwash, lozenge or lollipop.

The thiazolindblinone compound of the present invention has the ability to crystallize in more than one form, a characteristic known as polymorphism, and all such polymorphic forms ("polymorphs") are encompassed within the scope of the invention. Polymorphism generally can occur as a response to changes in temperature or pressure or both, and can also result from variations in the crystallization process. Polymorphs can be distinguished by various physical characteristics, and typically the x-ray diffraction patterns, solubility behavior, and melting point of the compound are used to distinguish polymorphs.

As used herein, the phrase "in the vicinity of" in reference to a specified value of melting point temperature means a temperature (measured in degrees Centigrade) in the range of the specified value ±2° C.

In the ensuing description, reagents employed in the synthesis of the invention are commercially available or are prepared according to procedures in the literature. The physical data given for the compounds exemplified is consistent with the assigned structure of those compounds. $^1$H NMR spectra were obtained on Varian Unity Plus NMR spectrophotometers at 300 or 400 Mhz. Mass spectra were obtained on Micromass Platform II mass spectrometers from Micromass Ltd., Altrincham, UK, using either atmospheric chemical ionization (APCI) or Electrospray Ionization (ESI). Analytical thin layer chromatography (TLC) was used to verify the purity of some intermediates which could not be isolated or which were too unstable for full characterisation, and to follow the progress of the reactions. Unless otherwise stated, this was done using silica gel (Merck Silica Gel 60 F254). Unless otherwise stated, column chromatography for the purification of compounds used Merck Silica Gel 60 (230–400 mesh), and the stated solvent system under pressure.

Melting points were determined for the respective forms of the thiazolindolinone compound of the invention by using differential scanning calorimetry with a TA model 2910. The sample mass was 1–3 mg in each instance. Each sample was contained in an aluminum crimped pan and was kept under a nitrogen purge at a flow rate of 40 milliliters/minute. The heating rate was 10° C./minute.

Recrystallization procedures for the respective forms were carried out in each case with the compound being dissolved in the selected solvent and stored at ambient temperature (e.g., 25° C.) until the solvent evaporated. The solid residue was then analyzed by x-ray diffraction.

In the respective anti-solvent determinations, the compound was dissolved in a selected solvent at 25° C., and water or alcohol was added to precipitate a solid. The solid was analyzed by x-ray diffraction.

In the procedure for powder x-ray diffraction analysis, the powdered compound was sprinkled on a quartz zero background plate and scanned from 5–40° 2-Theta using a Scintag PADV or XDS2000.

Specific forms of the thiazolindolinone compound of the invention illustratively described hereinafter are denoted for ease of reference as Form A, Form B and Form C, respectively.

Form A

Form A is a thiazolindolinone compound with the formula:

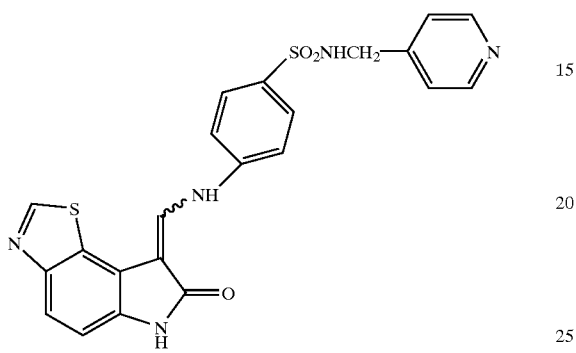

that may be variously characterised by its melting point, x-ray diffraction crystallographic spectral characteristics, solubilities in solvent media, anti-solvent character, and method of synthesis.

The melting point of Form A determined by the previously described melting point determination procedure is 235° C.

When the thiazolindolinone compound of the invention was dissolved in ethyl acetate, and the solution was cooled to 5° C., Form A was precipitated.

The solubilities (in milligrams per milliliter, mg/mL) of the Form A compound in polyethylene glycol 400, transcutol and methanol solvents are as follows:

| Solvent | Solubility |
|---|---|
| PEG 400 | 4.76 mg/mL |
| transcutol | 3.15 mg/mL |
| methanol | 0.30 mg/mL |

When subjected to slurry equilibration in which the Form A compound was added to acetone, n-butanol or methylene chloride to form a suspension equilibrated at 25° C. and analyzed by powder x-ray diffraction, no change in form resulted from the equilibration.

In anti-solvent characterisation, the precipitation of the thiazolindolinone compound of the invention from dimethyl sulfoxide using either water or alcohol as anti-solvent produced Form A.

BRIEF DESCRIPTION OF FIG. 1

X-ray diffraction characterisation of Form A showed such polymorph to have the x-ray diffraction spectra shown in FIG. 1 (spectra A1 and curve A2), wherein the respective curves are generated from different lots of the compound. X-ray diffraction values of Form A are tabulated below in Table I.

TABLE I

X-ray diffraction characteristics for Form A:
2-Theta and Relative Intensity Values

| 2-Theta | Relative Intensity |
|---|---|
| 2.84 | 5 |
| 3.12 | 3 |
| 3.46 | 4 |
| 3.58 | 3 |
| 3.64 | 3 |
| 3.80 | 4 |
| 3.97 | 5 |
| 6.49 | 40 |
| 7.08 | 79 |
| 10.75 | 14 |
| 12.01 | 100 |
| 12.78 | 54 |
| 14.19 | 16 |
| 15.37 | 4 |
| 16.44 | 36 |
| 17.38 | 13 |
| 17.69 | 36 |
| 18.00 | 33 |
| 18.76 | 13 |
| 19.52 | 36 |
| 20.77 | 4 |
| 21.19 | 9 |
| 21.36 | 15 |
| 21.59 | 10 |
| 21.80 | 11 |
| 22.79 | 39 |
| 23.12 | 75 |
| 24.00 | 23 |
| 24.61 | 14 |
| 25.42 | 31 |
| 27.78 | 24 |
| 28.92 | 12 |
| 31.90 | 4 |
| 35.82 | 3 |
| 35.99 | 4 |

Form B

Form B is a thiazolindolinone compound with the formula:

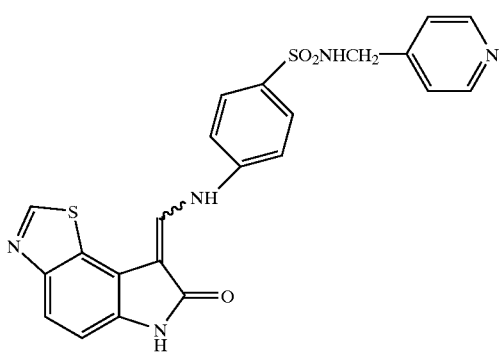

that may be variously characterized by its melting point, x-ray diffraction crystallographic spectral characteristics, solubilities in solvent media, and method of synthesis.

The melting point of Form B determined by the previously described melting point determination procedure is 247° C.

The solubilities (in milligrams per milliliter, mg/mL) of Form B in polyethylene glycol 400, transcutol and methanol solvents are as follows:

| Solvent | Solubility |
|---|---|
| PEG 400 | 4.5 mg/mL |
| transcutol | 2.77 mg/mL |
| methanol | 0.08 mg/mL |

X-ray diffraction characterisation of Form B showed such polymorph to have the x-ray diffraction spectra shown in FIG. 1 (spectrum B). X-ray diffraction values of Form B are tabulated below in Table II.

TABLE II

X-ray diffraction characteristics for Form B:
2-Theta and Relative Intensity Values

| 2-Theta | Relative Intensity |
|---|---|
| 6.75 | 13 |
| 7.00 | 33 |
| 11.54 | 7 |
| 12.00 | 72 |
| 13.51 | 36 |
| 14.06 | 14 |
| 16.14 | 37 |
| 17.67 | 27 |
| 18.23 | 32 |
| 18.54 | 8 |
| 18.89 | 18 |
| 20.35 | 21 |
| 21.19 | 22 |
| 21.61 | 12 |
| 23.12 | 14 |
| 24.28 | 14 |
| 24.83 | 1 |
| 25.72 | 3 |
| 26.69 | 100 |
| 27.32 | 5 |
| 28.61 | 2 |
| 28.81 | 2 |
| 30.22 | 2 |
| 30.35 | 2 |
| 30.77 | 1 |
| 31.08 | 1 |
| 31.67 | 1 |
| 33.62 | 2 |
| 35.15 | 1 |
| 35.70 | 4 |
| 35.97 | 1 |
| 36.94 | 2 |
| 37.64 | 1 |
| 38.36 | 3 |
| 40.99 | 1 |
| 42.47 | 1 |
| 42.68 | 3 |
| 44.88 | 1 |

Form C

Form C is a thiazolindolinone compound with the formula:

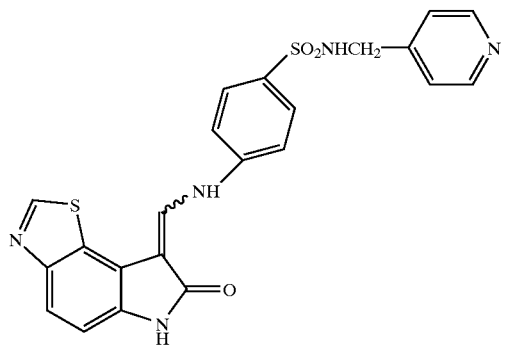

that may be variously characterised by its melting point, x-ray diffractioni crystallographic spectral characteristics, anti-solvent character, and method of synthesis.

The melting poinit of Form C determined by the previously described melting point determination procedure is 243° C.

In anti-solvent characterisation, the precipitation of the thiazolindolinone compound of the inventibn from N-methylpyrrolidone using either water or alcohol as anti-solvent produced Form C.

BRIEF DESCRIPTION OF FIG. 2

Figure 2:
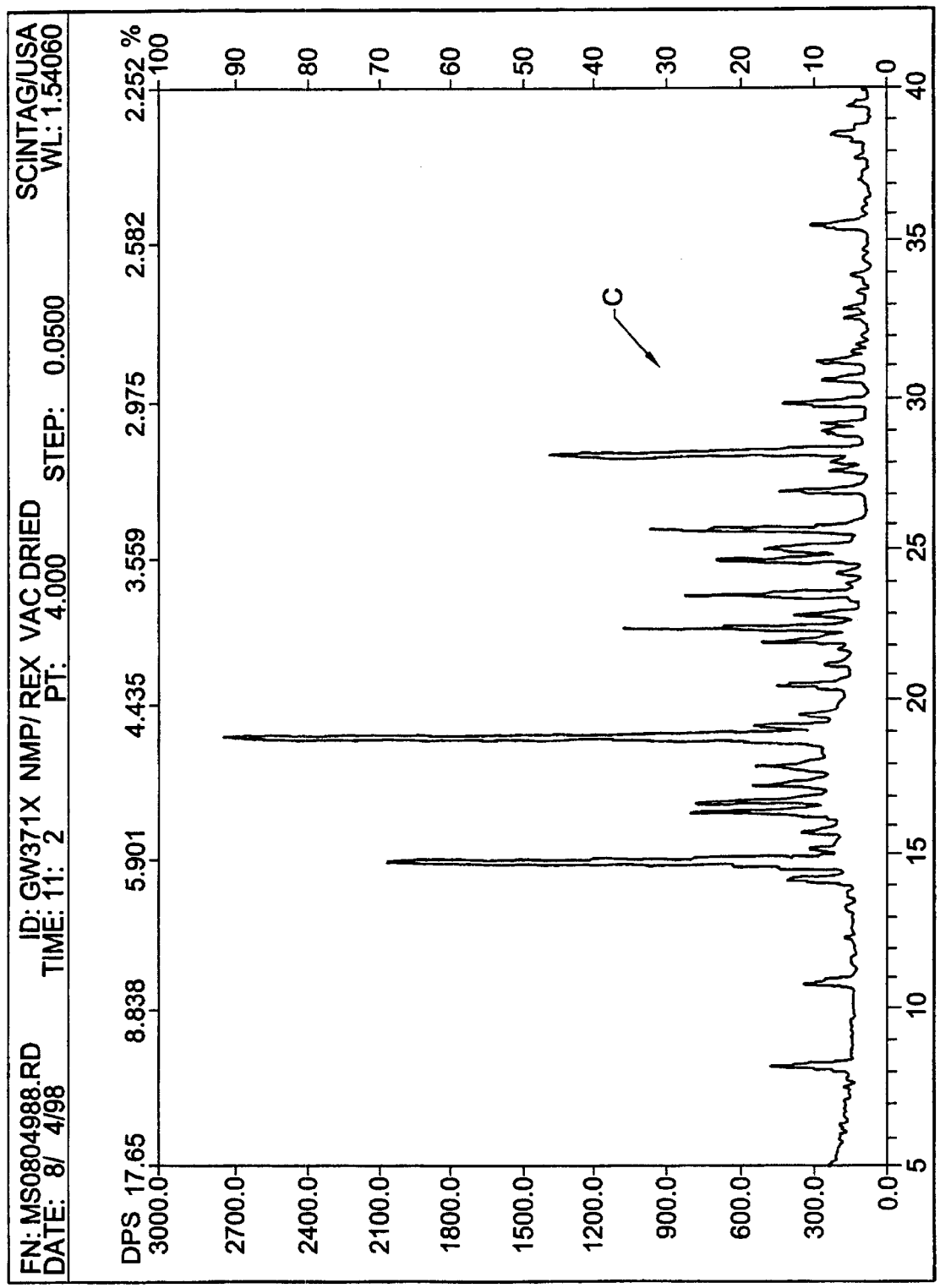

X-ray diffraction characterization of Form. C showed such form of the Compound to have the x-ray diffraction spectra shown in FIG. 2 (curve C). X-ray diffraction values for Form C are tabulated below in Table III.

TABLE III

X-ray diffraction characteristics for Form C:
2-Theta and Relative Intensity Values

| 2-Theta | Relative Intensity |
|---|---|
| 12.88 | 21 |
| 13.64 | 49 |
| 14.66 | 22 |
| 16.63 | 9 |
| 17.69 | 76 |
| 18.08 | 17 |
| 18.68 | 43 |
| 19.15 | 87 |
| 19.70 | 9 |
| 20.27 | 39 |
| 20.60 | 28 |
| 20.96 | 37 |
| 22.04 | 100 |
| 24.02 | 58 |
| 24.68 | 31 |
| 25.37 | 17 |
| 26.64 | 34 |
| 28.69 | 30 |
| 29.60 | 29 |
| 30.30 | 7 |
| 31.10 | 10 |
| 31.52 | 12 |
| 31.84 | 10 |
| 33.16 | 9 |
| 33.62 | 8 |
| 35.77 | 6 |
| 36.41 | 15 |

The features of the invention are more fully appreciated with respect to the following non-limiting examples.

EXAMPLE 1

Preparation of 4-Amino-N-(4-aminomethylpyridinyl) benzene-sulfonamide

To a 250 ml round bottom flask was added 50 ml of dry pyridine, 4-(aminomethyl) pyridine (10.4 g, 50.0 mmol) and a magnetic stir bar. The mixture was stirred and cooled to 0° C. under nitrogen followed by the addition of N-acetylsulfanilyl chloride (12.8 g, 55.0 mmol). The resultant mixture was stirred at 0° C. under nitrogen for 5 min, and the reaction was allowed to warm to room temperature and stirred for 16 hours. The reaction mixture was concentrated to a thick residue and poured onto about 500 g of ice and water. The residue in the flask was rinsed into the ice and water with 25 ml of MeOH to precipitate the N-acetyl sulfanilamide. The resultant precipitate was filtered, washed with excess water and dried under vacuum at 50° C. The solid was suspended in 75 ml of 1N hydrochloric acid and heated to 100° C. until all starting material had been consumed. The reaction mixture was cooled and neutralized with ammonium hydroxide. The precipitate was filtered and dried under vacuum at 50° C. to yield 5.78 g, 43.9% of the compound: $^1$H NMR (DMSO-d$_6$): δ 8.42 (d, 2H), 7.76 (t, 1H), 7.39 (d, 2H), 7.22 (d, 2H), 6.56 (d, 2H), 5.91 (s, 2H), 3.89 (d, 2H); APCI-MS m/z 264 (MH)$^+$.

EXAMPLE 2

Preparation of 6,8-Dihydro-7H-[1,3]thiazolo[5,4-e]indol-7-one

A 2-L three-neck round bottom flask was fitted with an internal thermometer, 250-mL addition funnel, magnetic stir bar and septa. The flask was charged with nitrogen, 200 mL of dry THF, and 6-aminobenzothiazole (15.2 g, 0.100 mol). The mixture was stirred and cooled in a dry ice-acetone bath to an internal temperature of −74° C. A solution of tert-butyl hypochlorite (11.0 g, 0.103 mol) in 50 mL of dichloromethane was added over a 15 minute period. The resultant solution was stirred for an additional 3 hours at dry ice-acetone bath temperature. To the reaction was then added by slow, dropwise addition a solution of ethyl methylthioacetate (13.8 g, 0.103 mol) in 50 mL of dichoromethane. The resultant solution was stirred for an additional 3 hours at dry ice-acetone bath temperature. A solution of triethyl amine (25.3 g, 0.250 mol) and 50 ml of dichloromethane was added at dry ice-acetone bath temperature, and the solution was stirred for 0.5 hours. The cooling bath was removed, and the reaction was allowed to warm to room temperature. The reaction was then concentrated to a thick residue. The thick oil was resuspended in 200 mL of ether and 600 mL of 0.25 M hydrochloric acid. The mixture was allowed to stir for 24 h. The resulting solid was filtered from the mixture and triturated with water and ether. The solid was then resuspended in cold MeOH, filtered and dried under vacum for 16 hours to yield 18.7 g (79%) of 8-(methylsulfanyl)-6,8-dihydro-7H-[1,3]thiazolo[5,4-e]indol-7-one: $^1$H NMR (DMSO-d6)δ 10.8 (s, 1H), 9.2 (s, 1H), 8.0 (d, 1H), 7.1 (d, 1H), 1.8 (s, 3H); APCI-MS m/z 235 (M-H). To a 500-mL Erlenmeyer flask was added a stir bar, 8.1 g (0.034 moles) of 8-(methylsulfanyl)-6,8-dihydro-7H-[1,3]thiazolo[5,4-e]indol-7-one and 100 mL of glacial acetic acid. The mixture was stirred until all the starting material had dissolved. The reaction mixture was then diluted with 100 mL of THF. Zinc metal (16 g, 325 mesh) was then added. The heterogeneous mixture was then stirred and heated to 60° C. for 2.5 hours. The mixture was vacuum filtered through a one half-inch pad of celite. The residue on the filter pad was washed with additional THF. The filtrates were combined and concentrated to a wet solid. The solid was triturated with MeOH, filtered and air dried to yield 4.51 g (70%) of the compound as a free-flowing solid: $^1$H NMR (DMSO-d6): δ 10.5 (s, 1H), 9.1 (s, 1H), 7.9 (d,;1H), 7.0 (d, 1H), 3.6 (s, 2H); APCI-MS m/z 191 (M+H)$^+$.

EXAMPLE 3

Preparation of 8-[Ethoxymethylidene]-6H-[1,3]thiazolo[5,4-e]indol-7-one

To a 250-ml round bottom flask was added a stir bar, 6,8-dihydro-7H-[1,3]thiazolo[5,4-e]indol-7-one (4.0 g, 0.021 mol), 40 mL of glacial acetic and diethoxymethyl acetate (17.0 g, 0.105 moles). The flask was fitted with a reflux condensor and charged with nitrogen. The reaction was heated to reflux for 8 h. The flask was cooled, the stir bar was removed and the reaction was concentrated to a wet solid. The solid was triturated with a solution of ether and ethanol. The mixture was filtered, and the solid was washed with an ethanol-ether solution and was dried under vacuum to yield the title compound: $^1$H NMR (DMSO-d6):δ 10.5 (s, 1H), 9.1 (s, 1H), 7.8 (d, 1H), 7.7 (s, 1H), 7.0 (d, 1H), 4.5 (q, 2H), 1.4 (t, 3H); APCI-MS m/z 245 (M-H)$^-$.

EXAMPLE 4

Form A—Preparations of 4-{[(7-oxo-6,7-dihydro8H-[1,3]thiazolo[5,4-e]indol-8-ylidene)methyl]amino}-N-(4-pyridinylmethyl)-benzenesulfonamide a) A mixture of 6.91 grams (28.0 mmol) of 8-[ethoxymethylidene] H=[1,3]thiazolo[5,4-e]indol-7one and 7.52 grams (28.0 mmol) of 4-amino-N-(4-pyridinylmethyl)benzenesulfonamide in 150 ml of ethanol was heated to reflux for 22 hours. The warm mixture was filtered, and the solid was air dried and washed with 300 ml of hot ethanol. The filter cake was dried under high vacuum at room temperature for 48 hours to obtain the thiazolindolinone compound as a yellow solid (11.0 grams, 85%): $^1$H NMR (DMSO-d$_6$): δ 4.02 (d,J=6.4 Hz, 2H), 7.11 (d,J=8.4 Hz, 1H), 7.24 (d,J=5.7 Hz, 2H), 7.56 (d,J=8.8 Hz, 2H), 7.77 (d,J=8.6 Hz, 2H), 7.81 (d,J=8.4 Hz, 1H), 8.05 (d,J=12.1 Hz, 1H), 8.24 (t,J=6.3 Hz, 1H), 8.44 (d,J=5.8 Hz, 2H), 9.26 (s, 1H), 10.92 (s, 1H), 11.15 (d,J=12.1 Hz, 1H); Analytically calculated: $C_{22}H_{17}N_5S_2O_3 \cdot 0.25 H_2O$; C, 56.46; H, 14.96; S. 13.70; Found: C, 56.41; H, 3.72; N, 14.89; S, 13.77.

b) A 3-necked round-bottom flask equipped with a paddle stirrer, temperature probe, and condenser was charged with 329 grams (1.25 moles) of 8-[ethoxymethylidene]-6H-[1,3]thiazolo[5,4-e]indol-7-one, 293 grams (1.19 moles) of 4-amino-N-(4-pyridinylmethyl)benzenesulfonamide, and 15540 milliliters of absolute alcohol. The light orange-red slurry was heated at gentle reflux (77–78° C.) for 27 hours to produce a dark brick-red slurry. The brick-red solid was isolated by filtration with the aid of 1500 milliliters of hot ethanol. The solid cake was stirred with a spatula and washed with three 1000-milliliter portions of boiling ethanol. The solid was transferred to a drying tray and dried under vacuum at 50–60° C. for 12 hours. The solid was gently strirred and dried an additional 20 hours in a vacuum oven at 60° C. Analytically calculated: $C_{22}H_{17}N_5O_3S_2 \cdot 0.20 C_2H_6O$; C, 56.91; H, 3.88; N, 14.81; S, 13.57; Found: C, 56.22; H, 3.87; N, 14.77; S, 13.77.

c) To a test tube (20 mm by 150 mm) was added a magnetic stir bar, 8-[ethoxymethylidene]-6H-[1,3]thiazolo[5,4-e]

indol-7-one (0.123 gram, 0.5 mmol), 4-amino-N-(4-pyridinylmethyl)benzenesulfonamide (0.132 gram, 0.5 mmol) and 95% ethanol (5 milliliters). The reaction mixture was sealed with a rubber septum (14/22) and vented with a 3-inch 18-gauge hypodermic needle. The reaction vessel was placed in an oil bath at room temperature with stirring, and the temperature of the oil bath was then raised to 78° C. and maintained at that temperature for approximately 24 hours. The reaction vessel was removed from the oil bath and allowed to cool until warm to the touch. The resulting precipitate was collected by suction filtration. The solid was washed with excess 95% ethanol and collected by suction filtration. The resultant solid was dried under vacuum for two hours at 40° C. The solid was allowed to cool to yield 52 mg (11%) of the title compound. MS (M+H)=464.

EXAMPLE 5

Form B—Preparations of 4-{[(7-oxo-6,7-dihydro-8H-[1,3]thiazolo[5,4-e]indol-8-ylidene)methyl]amino}-N-(4-pyridinylmethyl)-benzenesulfonamide a) A mixture of 51.0 grams (207 mmol) of 8-[ethoxymethylidene]-6H-[1,3]thiazolo[5,4-e]indol-7-one and 57.1 grams (217 mmol) of 4-amino-N-(4-pyridinylmethyl)benzenesulfonamide in 1.2 liters of ethanol was heated to reflux for 22 hours. The mixture was concentrated almost to dryness by distilling off the ethanol. The concentrated residue was diluted with 800 ml of ethanol and warmed to 80° C. for 1 hour. The warm mixture was filtered, and the solid was washed with ethanol. The filter cake was dried under high vacuum at room temperature to afford the thiazolindolinone compound as a yellow solid (88.9 grams, 93%): $^1$H NMR (DMSO-$d_6$): δ 4.02 (d,J=6.4 Hz, 2H), 7.11 (d,J=8.4 Hz, 1H), 7.24 (d,J=5.7 Hz, 2H), 7.56 (d,J=8.8 Hz, 2H), 7.77 (d,J=8.6 Hz, 2H), 7.81 (d,J=8.4 Hz, 1H), 8.05 (d,J=12.1Hz, 1H), 8.24 (t,J=6.3 Hz, 1H), 8.44 (d,J=5.8 Hz, 2H), 9.26 (s, 1H), 10.92 (s, 1H) 11.15 (d,J=12.1Hz, 1H); Analytically calculated: $C_{22}H_{17}N_5S_2O_3$. 0.25 $H_2O$ . 0.02 $C_2H_6O$: C, 56.45; H, 3.79; N, 14.93; S, 13.68; Found: C, 56.47; H, 3.78; N, 14.71; S, 13.80.

b) To a 250-ml round bottom flask was added a magnetic stir bar, 8-[ethoxymethylidene]-6H-[1,3]thiazolo[5,4-e]indol-7-one (1.98 grams, 8.05 mmol), 4-amino-N-(4-pyridinylmethyl)benzenesulfonamide (2.16 grams, 8.2 mmol) and 95% ethanol (80 ml). The round bottom reaction flask was fitted with a water cooled reflux condenser. The reaction vessel was placed in an oil bath at room temperature with stirring and the temperature of the oil bath was then raised to a gentle reflux and maintained at that temperature for approximately 36 hours. The reaction vessel was removed from the oil bath and the hot mixture was filtered with the solids being collected by suction filtration. The resultant solid was washed with excess 95% ethanol and collected by suction filtration. The solid was then dried under vacuum for two days at room temperature to yield 2.785 grams (74.7%) of the thiazolindolinone compound. MS (M+H)=464.

EXAMPLE 6

Preparation of a Mixture of Form A and Form B of 4-{[(7-oxo-6,7-dihydro-8H-[1,3]thiazolo[5,4-e]indol-8-ylidene)methyl]amino}-N-(4-pyridinylmethyl) benzenesulfonamide To a 250-ml round bottom flask was added a magnetic stir bar, 8-[ethoxymethylidene-6H-[1,3]thiazolo[5,4-e]indol-7-one (4.11 grams, 17.12 mmol), 4-amino-N-(4-pyridinylmethyl)benzenesulfonamide (4.62 grams, 17.55 mmol) and 95% ethanol (150 ml). The round bottom flask was fitted with a water-cooled reflux condenser. The reaction vessel was placed in an oil bath at room temperature with stirring, and the temperature of the oil bath was then raised to a gentle reflux and maintained at that temperature for approximately 48 hours. The reaction vessel was removed from the oil bath, and the hot mixture was filtered with the solids being collected by suction filtration. The resultant solid was washed with excess 95% and collected by suction filtration. The solid was then dried under vacuum for two days at room temperature to yield 5.143 grams (64.8%) of the thiazolindolinone compound. MS (M+H)=464.

EXAMPLE 7

The compound 4-(((7-oxo-6,7-dihydro-8H-[1,3]thiazolo[5,4-e]indol-8-ylidene)-methyl)amino)-N-(4-pyridinylmethyl) benzenesulfonamide was subjected to crystallization determinations using various solvents and methods of crystallization as described in Table IV below.

TABLE IV

Crystallization Determinations

| Crystallization Solvent | Initial Form | Method of Crystallization | Final Form | Comments |
|---|---|---|---|---|
| DMSO | Form A | Evaporation at 25° C. | Form A | evaporation very slow |
| DMSO | Form A | Water as antisolvent at 25° C. | Form A | |
| DMSO | Form A | Water as antisolvent at 37° C., then cooled to 25° C. | Form A | |
| DMSO | Form A | Alcohol as antisolvent at 25° C. | Form A | |
| DMSO | Form A | Alcohol as antisolvent at 37° C., then cooled to 25° C. | Form A | |
| Pyridine | Form A | Evaporation at 25° C. | Form A | Solubility low |
| DMF | Form B | Evaporation at 25° C. | Form A | |
| Ethyl acetate | Form B | Evaporation at 25° C. | Form A | Solubility low |
| Ethyl acetate | Form A | Cooling at 5° C. | Form A | (less than 0.06 mg/mL) |
| N-methyl-pyrrolidone | Form B | Water as antisolvent at 25° C. | Form C | Confirmed by PXRD |
| n-Butanol | Form A | Slurry equilibration at 25° C. | Form A | |
| Acetone | Form A | Slurry equilibration at 25° C. | Form A | |
| Methylene chloride | Form A | Slurry equilibration at 25° C. | Form A | |
| Tetrahydrofuran | Form A | Evaporation at 25° C. | Form A | |
| PEG 400 | Form A | Water as antisolvent at 25° C. | Form A + B | |

TABLE IV-continued

Crystallization Determinations

| Crystallization Solvent | Initial Form | Method of Crystallization | Final Form | Comments |
|---|---|---|---|---|
| PEG 400 | Form A | Alcohol as antisolvent at 25° C. | Form A + B | |

In Table IV, DMSO=dimethylsulfoxide; DMF=dimethylformamide; and PEG 400=polyethylene glycol having a molecular weight of 400; PXRD=powder x-ray diffraction.

In the case of solvent that are relatively non-volatile (DMSO, DMF), complete evaporation was difficult to achieve at 250° C. The presence of solvent was evident as an amorphous hump in the PXRD pattern. Cooling at 5° C. was less successful than the other crystallization approaches as a consequence of the low solubility of 4-(((7 oxo-6,7-dihydro-8H [1,3]thiazolo[5,4-e]indol-8-ylidene)methyl) amino)-N-(4-pyridinylmethyl) benzenesulfonamide under such conditions.

While the invention has been described herein with respect to various illustrative aspects, features and embodiments, it will be appreciated that the invention is susceptible of embodiment in other variations, modifications and specific embodiments of its disclosed features. Accordingly, the invention is intended to be broadly interpreted and construed, as including all such variations, modifications and other embodiments, within its spirit and scope as hereinafter claimed.

The application of which this description and claim(s) forms part may be used as a basis for priority in respect of any subsequent application. The claims of such subsequent application may be directed to any feature or combination of features described herein. They may take the form of product, formulation, process or use claims and may include, by way of example and without limitation, one or more of the following claim(s):

What is claimed is:

1. A thiazolindolinone compound of the formula:

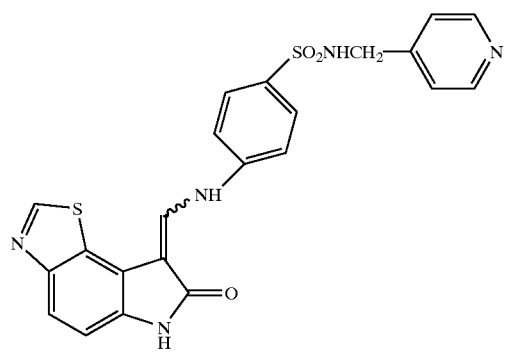

characterised by a melting point in the vicinity of 235° C.

2. A thiazolindolinone compound of the formula as defined in claim 1 having an x-ray diffraction spectrum equivalent to a spectrum (A1 and A2) of FIG. 1.

3. A thiazolindolinone compound of the formula as defined in claim 1 having the following solubility characteristics:

| Solvent | Solubility |
|---|---|
| PEG 400 | 4.76 mg/mL |
| transcutol | 3.15 mg/mL |
| methanol | 0.30 mg/mL. |

4. A thiazolindolinone compound of the formula as defined in claim 1 having the following x-ray diffraction characteristics:

| 2-Theta | Relative Intensity |
|---|---|
| 2.84 | 5 |
| 3.12 | 3 |
| 3.46 | 4 |
| 3.58 | 3 |
| 3.64 | 3 |
| 3.80 | 4 |
| 3.97 | 5 |
| 6.49 | 40 |
| 7.08 | 79 |
| 10.75 | 14 |
| 12.01 | 100 |
| 12.78 | 54 |
| 14.19 | 16 |
| 15.37 | 4 |
| 16.44 | 36 |
| 17.38 | 13 |
| 17.69 | 36 |
| 18.00 | 33 |
| 18.76 | 13 |
| 19.52 | 36 |
| 20.77 | 4 |
| 21.19 | 9 |
| 21.36 | 15 |
| 21.59 | 10 |
| 21.80 | 11 |
| 22.79 | 39 |
| 23.12 | 75 |
| 24.00 | 23 |
| 24.61 | 14 |
| 25.42 | 31 |
| 27.78 | 24 |
| 28.92 | 12 |
| 31.90 | 4 |
| 35.82 | 3 |
| 35.99 | 4. |

5. A thiazolindolinone compound formed by dissolution in a crystallization solvent of a compound of the formula as defined in claim 1 and evaporation of the solvent at ambient temperature to yield said thiazolindolinone compound as a crystalline solid, wherein the crystallization solvent is selected from the group consisting of dimethylformamide, dimethylsulfoxide, pyridine, ethyl acetate, and tetrahydrofuran.

6. A compound formed by dissolution in dimethyl sulfoxide of a compound of the formula as defined in claim 1 and addition to the resulting solution of a reagent selected from water and alcohols in an amount effective to precipitate said compound.

7. A compound formed by dissolution in ethyl acetate of a compound of the formula as defined in claim 1 and cooling of the resulting solution to form a precipitate as said thiazolindolinone compound.

8. Form A of 4-{[(7-oxo-6,7-dihydro-8H-[1,3]thiazolo[5,4-e]indol-8-ylidene)-methyl]amino}N-(4-pyridinylmethyl)-benzenesulfonamide.

9. A pharmaceutical composition comprising Form A of 4-{[(7-oxo-6,7-dihydro-8H-[1,3]thiazolo[5,4-e]indol-8-ylidene)methyl]amino}-N-(4-pyridinyl-methyl)benzenesulfonamide.

10. A pharmaceutical composition comprising an amount of Form A of 4-{[(7-oxo-6,7-dihydro-8H-[1,3]thiazolo5,4-e]indol-8-ylidene)methyl]-amino}-N-(4-pyridinylmethyl)benzene-sulfonamide that is effective to prevent/reduce the severity of epithelial cell toxicity induced by the administration of chemotherapy and/or radiation therapy when said composition is topically applied to an epithelial locus of epithelial cell toxicity.

11. A thiazolindolinone compound of the formula as defined in claim 1 characterised by a melting point in the vicinity of 247° C.

12. A thiazolindolinone compound of the formula as defined in claim 1 having an x-ray diffraction spectrum equivalent to a spectrum (B) of FIG. 1.

13. A thiazolindolinone compound of the formula as defined in claim 1 having the following solubility characteristics:

| Solvent | Solubility |
| --- | --- |
| PEG 400 | 4.5 mg/mL |
| transcutol | 2.77 mg/mL |
| methanol | 0.08 mg/mL. |

14. A thiazolindolinone compound of the formula as defined in claim 1 having the following x-ray diffraction characteristics:

| 2-Theta | Relative Intensity |
| --- | --- |
| 6.75 | 13 |
| 7.00 | 33 |
| 11.54 | 7 |
| 12.00 | 72 |
| 13.51 | 36 |
| 14.06 | 14 |
| 16.14 | 37 |
| 17.67 | 27 |
| 18.23 | 32 |
| 18.54 | 8 |
| 18.89 | 18 |
| 20.35 | 21 |
| 21.19 | 22 |
| 21.61 | 12 |
| 23.12 | 14 |
| 24.28 | 14 |
| 24.83 | 1 |
| 25.72 | 3 |
| 26.69 | 100 |
| 27.32 | 5 |
| 28.61 | 2 |
| 28.81 | 2 |
| 30.22 | 2 |
| 30.35 | 2 |
| 30.77 | 1 |
| 31.08 | 1 |
| 31.67 | 1 |
| 33.62 | 2 |
| 35.15 | 1 |
| 35.70 | 4 |
| 35.97 | 1 |
| 36.94 | 2 |
| 37.64 | 1 |
| 38.36 | 3 |
| 40.99 | 1 |
| 42.47 | 1 |
| 42.68 | 3 |
| 44.88 | 1. |

15. Form B of 4-{[(7-oxo-6,7-dihydro-8H-[1,3]thiazolo[5,4-e]indol-8-ylidene)-methyl]amino}-N-(4-pyridinylmethyl)-benzenesulfonamide.

16. A pharmaceutical composition comprising Form B of 4-{[(7-oxo-6,7-dihydro-8H-[1,3]thiazolo[5,4-e]indol-8-ylidene)methyl]amino}-N-(4-pyridinylmethylybenzene-sulfonamide.

17. A pharmaceutical composition comprising an amount of Form B of 4-{[(7-oxo-6,7-dihydro-8H-[1,3]thiazolo[5,4-e]indol-8-ylidene)methyl]amino}-N-(4-pyridin-ylmethyl)benzene-sulfonamide that is effective to prevent/reduce the severity of epithelial cell toxicity induced by the administration of chemotherapy and/or radiation therapy when said composition is topically applied to an epithelial locus of epithelial cell toxicity.

18. A thiazolindolinone compound of the formula as defined in claim 1 characterised by a melting point in the vicinity of 243° C.

19. A thiazolindolinone compound of the formula as defined in claim 1 having an x-ray diffraction spectrum (C) of FIG. 2.

20. A thiazolindolinone compound of the formula as defined in claim 1 having the following x-ray diffraction characteristics:

| 2-Theta | Relative Intensity |
| --- | --- |
| 12.88 | 21 |
| 13.64 | 49 |
| 14.66 | 22 |
| 16.63 | 9 |
| 17.69 | 76 |
| 18.08 | 17 |
| 18.68 | 43 |
| 19.15 | 87 |
| 19.70 | 9 |
| 20.27 | 39 |
| 20.60 | 28 |
| 20.96 | 37 |
| 22.04 | 100 |
| 24.02 | 58 |
| 24.68 | 31 |
| 25.37 | 17 |
| 26.64 | 34 |
| 28.69 | 30 |
| 29.60 | 29 |
| 30.30 | 7 |
| 31.10 | 10 |
| 31.52 | 12 |
| 31.84 | 10 |
| 33.16 | 9 |
| 33.62 | 8 |
| 35.77 | 6 |
| 36.41 | 15. |

21. A thiazolindolinone compound formed by dissolution in N-methylpyrrolidone of a compound of the formula as defined in claim 1 to form a resulting solution, and addition to the solution of an anti-solvent selected from the group consisting of water and alcohols, in sufficient amount to yield a precipitate as said thiazolindolinone compound.

22. Form C of 4-{[(7-oxo-6,7-dihydro-8H-[1,3]thiazolo[5,4-e]indol-8-ylidene)-methyl]amino}-N-(4-pyridinylmethyl)-benzenesulfonamide.

23. A pharmaceutical composition comprising Form C of 4-{[(7-oxo-6,7-dihydro-8H-[1,3]thiazolo[5,4-e]indol-8-ylidene)methyl]amino}-N-(4-pyridinyl-methyl)benzene-sulfonamide.

24. A pharmaceutical composition comprising an amount of Form C of 4-{[(7-oxo-6,7-dihydro-8H-[1,3]thiazolo[5,4-e]indol-8-ylidene)methyl]amino}-N-(4-pyridin-ylmethyl)benzene-sulfonamide that is effective to prevent/reduce the severity of epithelial cell toxicity induced by the administration of chemotherapy and/or radiation therapy when said composition is topically applied to an epithelial locus of epithelial cell toxicity.

25. A method for preparing a thiazolindolinone compound of the formula as defined in claim 1 by conducting at least one synthesis step of synthesis Scheme 1 described herein to yield 4-{[(7-oxo-6,7-dihydro-8H-[1,3]thiazolo[5,4-e]indol-8-ylidene)-methyl]amino}-N-(4-pyridinylmethyl)-benzenesulfonamide as a synthesis reaction product;

subjecting said synthesis reaction product to a treatment thereof yielding one of Forms A, B and C of 4-{[(7-oxo-6,7-dihydro-8H-[1,3]thiazolo[5,4-e]indol-8-ylidene)methyl]amino}-N-(4-pyridinylmethyl)benzenesulfon-amide; and recovering same as said thiazolindolinone compound.

26. A method according to claim 25, wherein said treatment comprises dissolving said synthesis reaction product in a solvent to form a solution, and evaporating said solvent to recover the thiazolindolinone compound.

27. A method according to claim 26, wherein the solvent is selected from the group consisting of dimethylformamide, dimethylsulfoxide, pyridine, ethyl acetate and tetrahydrofuran, and said thiazolindolinone compound is of Form A.

28. A method according to claim 25, wherein said treatment comprises dissolving said synthesis reaction product in a solvent to form a solution, and cooling said solution to a sufficient extent to precipitate said thiazolindolinone compound.

29. A method according to claim 29, wherein said solvent is ethyl acetate, and said thiazolindolinone compound is of Form A.

30. A method according to claim 25, wherein said treatment comprises dissolving said synthesis reaction product in a solvent to form a solution, and adding an anti-solvent selected from the group consisting of water and alcohols to precipitate said thiazolindolinone compound.

31. A method according to claim 30, wherein the solvent is dimethylsulfoxide and said thiazolindolinone compound is of Form A.

32. A method according to claim 30, wherein the solvent is N-methpyrrolidone, said anti-solvent is water and said thiazolindolinone compound is of Form C.

33. A method according to claim 25, wherein said thiazolindolinone is of Form A.

34. A method according to claim 25, wherein said thiazolindolinone is of Form B.

35. A method according to claim 25, wherein said thiazolindolinone is of Form C.

36. A method of preventing/reducing the severity of epithelial cytotoxicity side-effects of chemotherapy and/or radiation therapy, in a subject receiving such therapy, by administering to the subject an effective amount of one or more of Forms A, B and C of 4-{[(7-oxo-6,7-dihydro-8H-[1,3]thiazolo[5,4-e]indol-8-ylidene)methyl]amino}-N-(4-pyridinylmethyl)-benzenesulfonamide.

37. A method according to claim 36, wherein Form A of 4-{[(7-oxo-6,7-dihydro-8H-[1,3]thiazolo[5,4-e]indol-8-ylidene)methyl]amino}-N-(4-pyridinylmethyl) benzenesulfonamide is administered to said subject.

38. A method according to claim 36, wherein Form B of 4-{[(7-oxo-6,7-dihydro-8H-[1,3]thiazolo[5,4-e]indol-8-ylidene)methyl]amino}-N-(4-pyridinylmethyl) benzenesulfonamide is administered to said subject.

39. A method according to claim 36, wherein Form C of 4-{[(7-oxo-6,7-dihydro-8H-[1,3]thiazolo[5,4-e]indol-8-ylidene)methyl]amino}-N-(4-pyridinylmethyl) benzenesulfonamide is administered to said subject.

40. A method according to claim 36, wherein the epithelial cytotoxicity side-effect comprises alopecia.

41. A method according to claim 36, wherein the epithelial cytotoxicity side-effect comprises plantar-paimar syndrome.

42. A method according to claim 36, wherein the epithelial cytotoxicity side-effect comprises mucositis.

43. A method according to claim 36, wherein the effective amount of one or more of Forms A, B and C of 4-{[(7-oxo-6,7-dihydro-8H-[1,3]thiazolo[5,4-e]indol-8-ylidene) methyl]amino}-N-(4-pyridinylmethyl)benzenesulfonamide is topically administered to the scalp to prevent/reduce the severity of chemotherapy-induced alopecia.

44. A method according to claim 36, wherein the effective amount of one or more of Forms A, B and C of 4-{[(7-oxo-6,7-dihydro-8H-[1,3]thiazolo[5,4-e]indol-8-ylidene) methyl]amino}-N-(4-pyridinylmethyl)benzenesulfonamide is topically administered to the hands and/or feet to prevent/reduce the severity of chemotherapy-induced plantar-palmar syndrome.

45. A method according to claim 36, wherein the effective amount of one or more of Forms A, B and C of 4-{[(7-oxo-6,7-dihydro-8H-[1,3]thiazolo[5,4-e]indol-8-ylidene) methyl]amino}-N-(4-pyridinylmethyl)benzene sulfonamide is topically administered to oral cavity mucosa to prevent/reduce the severity of chemotherapy-induced mucositis.

46. A method according to claim 36, wherein the effective amount of one or more of Forms A, B and C of 4-{[(7-oxo-6,7-dihydro8H-[1,3]thiazolo[5,4-e]indol-8-ylidene)methyl] amino}-N-(4-pyridinylmethyl)benzenesulfonamide is administered in a topically applied formulation to corporeal loci susceptible to incidence of epithelial cytotoxicity induced by chemotherapy and/or radiation therapy.

47. A pharmaceutical composition comprising a thiazolindolinone compound according to claim 1, and one or more pharmaceutically acceptable carriers, excipients or diluents.

48. A pharmaceutical composition comprising a thiazolindolinone compound according to claim 11 and one or more pharmaceutically acceptable carriers, excipients or diluents.

49. A pharmaceutical composition comprising a thiazolindolinone compound according to claim 18 and one or more pharmaceutically acceptable carriers, excipients or diluents.

50. A pharmaceutical composition comprising at least one of Forms A, B and C of 4-{[(7-oxo-6,7-dihydro-8H-[1,3] thiazolo[5,4-e]indol-8-ylidene)methyl]amino}-N-(4-pyridinylmethyl)benzenesulfonamide and one or more pharmaceutically acceptable carriers, excipients or diluents.

\* \* \* \* \*